United States Patent [19]

Shecterle et al.

[11] Patent Number: 5,623,945
[45] Date of Patent: Apr. 29, 1997

[54] DOUBLE LAYER PROPHYLACTIC INCORPORATING PHARMACOLOGICAL FLUID AND SPIRAL BARRIER LAYER

[75] Inventors: Linda M. Shecterle, Plymouth; John A. St. Cyr, Maple Grove, both of Minn.

[73] Assignee: Jacqmar, Inc., Plymouth, Minn.

[21] Appl. No.: 487,844

[22] Filed: Jun. 7, 1995

Related U.S. Application Data

[63] Continuation-in-part of Ser. No. 296,900, Aug. 29, 1994, abandoned.

[51] Int. Cl.⁶ ......................................................... A61F 6/02
[52] U.S. Cl. .............................. 128/842; 128/844; 128/918
[58] Field of Search ................................. 128/842, 844, 128/918; 604/347–353

[56] References Cited

U.S. PATENT DOCUMENTS

| | | | |
|---|---|---|---|
| 4,332,243 | 6/1982 | Gutnick | 128/844 |
| 4,910,803 | 3/1990 | Cukier | 128/844 |
| 4,930,522 | 6/1990 | Busnel | 128/844 |
| 5,045,341 | 9/1991 | Shlenker | 128/844 |

FOREIGN PATENT DOCUMENTS

| | | | |
|---|---|---|---|
| 0920172 | 10/1992 | WIPO | 128/918 |

*Primary Examiner*—Michael A. Brown
*Attorney, Agent, or Firm*—Haugen and Nikolai, P.A.

[57] ABSTRACT

A two layer prophylactic device taking the form of a male or female condom, or female diaphragm. The invention includes two latex layers bonded to one another along a spiral path which defines a corresponding spiral chamber between the latex layers. This spiral chamber extends between two compliant chambers at opposed ends of the device and is filled with a pharmacological fluid to help kill disease-bearing microbes and sperm cells which may permeate through the device during coitus. Due to the unique spiral chamber design leading between the complaint chambers, this pharmacological fluid remains uniformly dispersed during coitus and the device is less subject to rupture. Should one layer rupture during use, the pharmacological fluid will flow through the rupture and coat the adjacent sex organ. The present invention is especially effective in preventing unwanted pregnancies and the transmission of sexually transmitted diseases.

13 Claims, 1 Drawing Sheet

5,623,945

DOUBLE LAYER PROPHYLACTIC INCORPORATING PHARMACOLOGICAL FLUID AND SPIRAL BARRIER LAYER

I. CROSS REFERENCE TO RELATED APPLICATIONS

This is a continuation-in-part of application Ser. No. 08/296,900, filed Aug. 29, 1994, now abandoned and entitled "DOUBLE LAYER PROPHYLACTIC INCORPORATING PHARMACOLOGICAL FLUID AND SPIRAL BARRIER LAYER".

II. FIELD OF THE INVENTION

This invention is generally related to prophylactic devices for inhibiting the communication of contagious diseases during coitus, and more particularly to a male/female condom or diaphragm having an integral chamber containing a pharmacological fluid with anti-microbial, anti-viral, anti-bacterial and spermicidal properties.

III. BACKGROUND OF THE INVENTION

Today, the risk of communicating contagious diseases during coitus is as great as ever. Despite these risks, society will continue to engage in sexual activity, albeit with more precautions being taken to reduce these risks. It is not enough for one partner to simply ask the other whether they are carrying a contagious communicable disease, and a prudent person should take precautions to guard against these risks.

Perhaps some of the most feared diseases which can be spread during coitus include hepatitis, venereal diseases, and Acquired Immunodeficiency Syndrome, commonly known as AIDS. Both society and the medical industry continue to encourage the use of prophylactics during coitus to prevent the transmission of disease. Male and female condoms, and cervical blocks (diaphragms), are commonly available and well known prophylactics.

Despite using prophylactics, the risk still exists that a contagious disease can be communicated during coitus. This is primarily due to the fact that prophylactics are typically comprised of latex. On average, a thin latex membrane has pores or holes whose single size is in the micron range. Viruses such as AIDS are known to have microbes in the range of less than 1.0 microns, and hence, have the potential capability to pass through ordinary latex condoms. Therefore, additional pharmacological agents are required in combination with condoms to minimize or eliminate the risk of infection between partners. These pharmacological fluids have bactericidal, virucidal, and spermicidal properties and are commonly available. For example, butylurea is recognized as the most potent inhibitor of HIV-1, commonly known as the AIDS virus. Butylurea is from a group of chemicals known as the alkylureas, which are known to inhibit infectivity of free HIV and which kill the virus.

U.S. Pat. No. 4,930,522 to Busnel et al discloses a prophylactic device made of rupturable micro encapsulated elastomeric material. This device comprises two layers of the elastomeric material arranged one on top of the other, and having disposed therebetween microcapsules formed between rupturable walls. These microcapsules have enclosed therein at least one pharmacologically active substance.

U.S. Pat. No. 5,045,341 Shlenker, discloses a condom having an array of staggered chambers defined between two layers. These staggered chambers encapsulate a chemical barrier.

U.S. Pat. No. 4,332,243 Gutnick, discloses a condom having a septum wall formed with opposed indentations to provide easily burstable breach areas that will release medication inside the condom. A distal chamber carrying medication is intended to rupture or breach during intercourse to allow egress of the medication to coat the male organ. In another embodiment, a vaginal diaphragm or cervical cap is shown to accomplish the distribution of the medication.

U.S. Pat. No. 4,910,803 Cukier, teaches a two layer condom with an integral marker. This marker is positioned in relation to a wearer of the condom so that in the event of a breach in the first layer, the second layer is contacted by a marker fluid. The marker fluid reacts with a specific bodily fluid, and includes a color metric property to visually indicate the exposure to the body fluid. Thus, the user can ascertain whether or not a breach of the condom occurred during use.

OBJECTS

It is accordingly a principle object of the present invention to provide a prophylactic device which effectively reduces or prevents the transmission of diseases between partners during intercourse.

It is a further object of the present invention to provide a prophylactic device incorporating a pharmacological agent which further reduces the chance particular diseases can be transmitted between partners.

Still another object of the present invention is to provide a two layer condom having a chamber defined therebetween for storing a pharmacological agent, whereby this fluid will remain uniformly dispersed when the condom is deployed during coitus or other forms of heterosexual or homosexual activity.

Still yet another object of the present invention is to provide a prophylactic device which is easy and affordable to manufacture.

SUMMARY OF THE INVENTION

The foregoing objects are achieved by providing a two layer prophylactic device with these layers being bonded to one another along a spiral path to define a spiral path therebetween that extends between first and second compliant reservoirs located proximate a closed end and an open end of the device. This spiral path or interspace is filled with a pharmacological fluid which can flow between the two reservoirs when the condom is deployed during coitus and subjected to pressure forces. This pharmacological fluid can have anti-microbial, anti-viral, anti-bacterial and/or spermicidal properties. Should one layer of the condom rupture during use, the pharmacological agent will flow through the rupture to coat the adjacent sex organ.

In the preferred embodiment of the present invention, the prophylactic device comprises an inner and outer latex layer defining a pocket. These two latex layers are bonded to one another along a spiral path the define a corresponding spiral path between the layers. In the preferred embodiment, a pair of interlaced spiral bonds are provided to define a pair of corresponding spiral paths. These spiral paths are of uniform size, are continuous and extend from an annular reservoir at the end of the device adapted to receive the male organ, a vertex reservoir at its distal end. Since the HIV virus, in particular, has a microbe dimension smaller then the pore dimensions in conventional latex sheaths, the pharmacological agent, in combination with two latex layers, reduces the likelihood that the virus can traverse the barrier layers and intermediate pharmacologic agent between partners engaged in oral, anal or vaginal sex.

The present invention can take the form of a male or female condom, or in the form of a female diaphragm. The present invention is easy and affordable to manufacture. The spiral bond can be created by using conventional laser welding techniques. The pharmacological agent can be easily injected between the layers before or after the bonding procedure.

These and other objects will become apparent upon a detailed reading of the following description in view of the appended drawings, wherein like numeral designations refer to like elements.

DESCRIPTION OF THE PREFERRED EMBODIMENT

Figure 1:
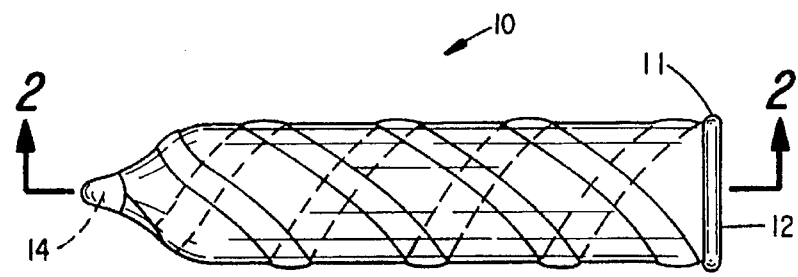
FIG. 1 is an elevational view of a male condom having two latex layers bonded to one another upon a spiral path, this bond defining a spiral chamber extending to a vertex reservoir.

Referring now to FIG. 1, a male condom according to the preferred embodiment of the present invention is generally shown at 10. Condom 10 has a first compliant reservoir 11 surrounding an opening 12 at one end, the opening adapted to fit about the male sex organ. The tubular sheath 13 extends to a vertex reservoir shown in phantom at 14 at the other (distal) end. It is to be recognized, however, that this invention could take the form of a female condom with minor modifications.

Figure 2:
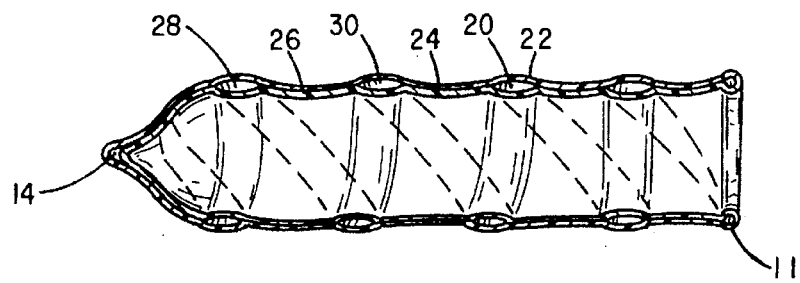
FIG. 2 is a cross-sectional view taken along line 2—2 in FIG. 1, illustrating the spiral bond and the spiral chamber storing a pharmacological agent.

Referring to FIG. 2, a cross-section of condom 10 taken along line 2—2 in FIG. 1 is shown. Condom 10 can be seen to include an inner latex layer 20 and an outer latex layer 22. Inner layer 20 is encompassed by and adjacent to outer layer 22, these layers together forming an elongated sheath, as shown. These two layers 20 and 22 are both comprised of liquid impermeable material, such as latex, and may be bonded to one another along a first spiral path 24 and a second spiral path 26. Paths 24 and 26 are interlaced, as shown. These paths may be achieved using conventional laser welding, but could be achieved through the use of an appropriate bonding agent, and limitation to a particular bonding technique is not to be inferred. Spiral paths 24 and 26, in turn, define a pair of interlaced spiral chambers or interspaces 28 and 30. Each of spiral chambers 28 and 30 is continuous, terminating at one end in the compliant annular chamber 11 proximate opening 12, and each extending to and communicating with vertex reservoir 14 at the distal end of condom 10. Each of chambers 28 and 30 is filled with a pharmacological fluid. This fluid has anti-microbial, anti-viral, anti-bacterial, and/or spermicidal properties. For example, butylurea could be used, and it is very effective in preventing the transmission of the AIDS virus.

The spiral chambers 28 and 30 are particularly effective in ensuring the pharmacological fluid residing therein remains uniformly dispersed. In other words, the chamber design ensures that the fluid is not likely to flow into a single pocket, especially when the condom is deployed during coitus. As the vertex chamber and/or the spiral paths are compressed, the fluid can flow to compliant reservoir 11 and, similarly, when the reservoir 11 is squeezed, the fluid may transfer to the reservoir 14, thereby lessening the likelihood of rupture. In addition, the spiral paths 24 and 26 helps ensure that the inner layer 20 does not become bunched up within outer layer 22. The proximal end of each layer 20 and 22 is bonded to one another along a circular periphery thereof, and then folded over to define a hollow chamber 11 around opening 12, as shown. To ensure adherence of the male condom of the present invention to the penis, it may be desirable to provide a relatively unaggressive adhesive on a portion of the inner surface thereof near the open end thereof. Such an adhesive should also be non-irritating to the skin and of a type that does not leave a residue following removal. Anecdotal evidence also suggests that the presence of the spiral ribs may heighten the degree of stimulation and arousal during intercourse.

By providing two latex layers, the probability of a virus propagating through pores in both layers is greatly reduced. In addition, the presence of the pharmacological agent helps kill any viruses which may attempt to propagate through the two latex layers. Should one or the other of the two latex layers rupture during use, the pharmacological fluid will flow one direction through the rupture to coat either the penis or the vagina, depending on which of the two layers ruptures.

The inclusion of a pharmacological agent is critical, especially to effectively prevent the spread of the HIV virus. Again, this is due to the fact that latex has pores, with the size of the pores ranging in microns, wherein the AIDS virus, in comparison, typically has microbes in the range of less than one micron. By implementing two latex layers, the pores of these layers remain statistically staggered along paths 24 and 26, whereby the virus is confronted by the pharmacological agent along spiral chambers 28 and 30.

Figure 3:
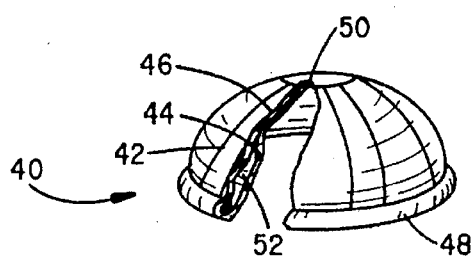
FIG. 3 is a partially sectioned perspective view of a female diaphragm according to an alternative preferred embodiment of the present invention.

Referring now to FIG. 3, an alternative embodiment of the present invention is shown as a female diaphragm generally at 40. Diaphragm 40 has many of the same characteristics as condom 10, the primary difference being that the pocket defined by the two latex layers is dome-shaped rather than tubular. Diagram 40 fits over a woman's cervical cap using a technique well know in the art. In this embodiment, a plurality of radially extending angular bonds 42 are provided to secure a pair a dome-shaped latex layers 44 and 46 together. Each of these latex layers is bonded together around a periphery, and folded over to form a hollow, compliant reservoir in the form of a rim or flange 48. A vertex reservoir 50 is provided at a centrally located portion atop diaphragm 40. Reservoir 50 is in fluid communication with each of a plurality of chambers 52 defined between the latex layers and with the reservoir 48, these chambers being connected by spiral path 52. A pharmacological fluid is provided in each of chambers 52 and reservoirs 48 and 50.

Similar to the male condom 10 shown in FIGS. 1 and 2, the pharmacological agent residing in chambers 52 remains rather uniformly dispersed when the diaphragm is deployed prior to coitus. Should one latex wall rupture, the pharmacological agent will then flow through the rupture to coat surfaces that may become exposed to body fluids. Again, because two latex layers are implemented in the present invention, the pores of the latex layers are statistically staggered or offset along bonds 42, decreasing the probability that a virus will penetrate both layers. The layers remain spatially separated along the fluid filled chambers 52, and the presence of the pharmacological agent, and the likelihood of a virus being transmitted through the two latex layers and remaining alive is slight.

Figure 4:
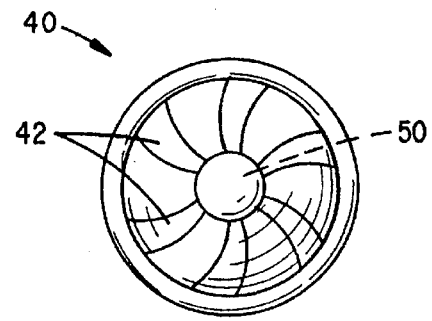
FIG. 4 is a top view of the female diaphragm of FIG. 3.

Diaphragm 40 is also easy and inexpensive to manufacture. The bonds 42 are preferably created using laser welding, but could also be achieved by use of adhesives and the like. The pharmacological agent is injected into chambers 52 and reservoirs 48 and 50 after forming bonds 42, but before bonding the periphery of the two layers to form compliant reservoir 48. FIG. 4 shows a top view of diaphragm 40 in FIG. 3. This figure illustrates the uniform and symmetric design of diaphragm 40. While six radially extending curved bonds 42 are shown and which define a corresponding number of chambers 52, limitation to the number of bonds and chambers chosen is not to be inferred.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A prophylactic device, comprising:
   (a) a first and a second layer of elastomeric, liquid impermeable material arranged adjacent one another and defining a pocket, said pocket having a vertex and an opposing rim, said first and second layers being bonded to one another along a continuous spiral path extending from a first compliant reservoir at said vertex to a second compliant reservoir at said rim to define an elongated spiral chamber of uniform cross-section communicating with the first and second reservoirs; and
   (b) a pharmacological agent disposed in said first and second reservoirs and said chamber.

2. The prophylactic device as specified in claim 1 wherein said first and second layers form a male condom, with said pocket being elongated and of a size to receive a penis therein.

3. The prophylactic device as specified in claim 1 wherein said first and second layers form a diaphragm, with said pocket being dome-shaped.

4. The prophylactic device as specified in claim 3 wherein said diaphragm has a plurality of said bonds radially extending from said second compliant reservoir at said rim to said first compliant reservoir at said vertex to define a plurality of said chambers therebetween.

5. The prophylactic device as specified in claim 1 wherein said pharmacological agent is selected from the group consisting of a spermicidal agent, a bactericidal agent, or a virucidal agent.

6. The prophylactic device as specified in claim 1 wherein said first and second layers are fused to one another along said continuous path.

7. The prophylactic device as specified in claim 1 wherein each said first and second layers are comprised of latex.

8. A prophylactic device, comprising:
   (a) a first and a second layer of elastomeric, liquid impermeable material arranged adjacent one another and defining a pocket, said pocket having a vertex and an opposing rim, said first and second layers being bonded to one another along a continuous pair of interlaced paths extending from a first compliant reservoir at said vertex to a second compliant reservoir at said rim to define a pair of interlaced chambers of uniform cross-section communicating with the first and second reservoirs; and
   (b) a pharmacological agent disposed in said first and second reservoirs and said chamber.

9. The prophylactic device as specified in claim 8 wherein said first and second layers form a male condom, with said pocket being elongated and of a size to receive a penis therein.

10. The prophylactic device as specified in claim 8 wherein said first and second layers form a diaphragm, with said pocket being dome-shaped.

11. The prophylactic device as specified in claim 8 wherein said pharmacological agent is selected from the group consisting of a spermicidal agent, a bactericidal agent, or a virucidal agent.

12. The prophylactic device as specified in claim 8 wherein said first and second layers are fused to one another along said continuous path.

13. The prophylactic device as specified in claim 8 wherein each said first and second layers are comprised of latex.

* * * * *